(12) United States Patent
Chandrashekhar et al.

(10) Patent No.: US 10,537,520 B2
(45) Date of Patent: Jan. 21, 2020

(54) STABLE LIQUID FORMULATIONS OF MELPHALAN

(71) Applicant: LEIUTIS PHARMACEUTICALS PVT. LTD., Hyderabad (IN)

(72) Inventors: Kocherlakota Chandrashekhar, Secunderabad (IN); Banda Nagaraju, Hyderabad (IN)

(73) Assignee: LEIUTIS PHARMACEUTICALS PVT. LTD., Telangana (IN)

( * ) Notice: Subject to any disclaimer, the term of this patent is extended or adjusted under 35 U.S.C. 154(b) by 0 days.

(21) Appl. No.: 15/739,034

(22) PCT Filed: Jun. 29, 2016

(86) PCT No.: PCT/IB2016/053881
§ 371 (c)(1),
(2) Date: Dec. 21, 2017

(87) PCT Pub. No.: WO2017/002030
PCT Pub. Date: Jan. 5, 2017

(65) Prior Publication Data
US 2018/0193255 A1    Jul. 12, 2018

(30) Foreign Application Priority Data
Jun. 30, 2015 (IN) .......................... 3328/CHE/2015

(51) Int. Cl.
*A61K 9/00* (2006.01)
*A61K 47/10* (2017.01)
*A61K 31/198* (2006.01)
*A61K 31/00* (2006.01)
*A61K 47/20* (2006.01)
*A61K 47/18* (2017.01)

(52) U.S. Cl.
CPC ............ *A61K 9/0019* (2013.01); *A61K 31/00* (2013.01); *A61K 31/198* (2013.01); *A61K 47/10* (2013.01); *A61K 47/18* (2013.01); *A61K 47/20* (2013.01)

(58) Field of Classification Search
None
See application file for complete search history.

(56) References Cited

U.S. PATENT DOCUMENTS

| 4,997,651 A | 3/1991 | Poole et al. |
| 2004/0055889 A1* | 3/2004 | Tran .......................... C25D 3/62 205/91 |
| 2008/0089940 A1* | 4/2008 | Omidian ................... A61K 9/06 424/487 |
| 2010/0311838 A1 | 12/2010 | Pipkin et al. |
| 2011/0166214 A1* | 7/2011 | Desu ...................... A61K 9/0019 514/449 |
| 2013/0131174 A1 | 5/2013 | Castillo et al. |
| 2014/0005148 A1 | 1/2014 | Neelakantan et al. |
| 2014/0213650 A1 | 7/2014 | Pipkin et al. |
| 2014/0221488 A1 | 8/2014 | Pipkin et al. |
| 2017/0020177 A1* | 1/2017 | Oguchi .................... A23L 27/60 |

FOREIGN PATENT DOCUMENTS

| EP | 0317281 | * 11/1988 |
| RU | 2060031 C1 | 5/1996 |
| WO | 2014178065 A1 | 11/2014 |

OTHER PUBLICATIONS

SciFinder, Thioglycerol, retrieved online on May 21, 2018 (Year: 2018).*
International Search Report and Written Opinion for PCT/IB2016/053881, dated Sep. 23, 2016.

* cited by examiner

*Primary Examiner* — Jennifer A Berrios
(74) *Attorney, Agent, or Firm* — Heslin Rothenberg Farley & Mesiti P.C.

(57) ABSTRACT

The present invention relates to stable, liquid parenteral formulations of Melphalan or pharmaceutically acceptable salts thereof. Further this invention also describes process of preparing such formulations.

4 Claims, No Drawings

STABLE LIQUID FORMULATIONS OF MELPHALAN

CROSS REFERENCE TO RELATED APPLICATIONS

This application is a U.S. National Phase filing under 35 U.S.C. § 371 of International Application PCT/IB2016/053881, filed Jun. 29, 2016, and published as WO 2017/002030 A1 on Jan. 5, 2017. PCT/IB2016/053881 claims priority from Indian application number 3328/CHE/2015, filed Jun. 30, 2015. The entire contents of each of these applications are hereby incorporated herein by reference.

BACKGROUND OF THE INVENTION

Melphalan, also known as L-phenylalanine mustard, L-PAM, or L-sarcolysin is a phenylalanine derivative of nitrogen mustard. Melphalan is a bifunctional alkylating agent that is active against selected human neoplastic diseases. The molecular formula is $C_{13}H_{18}Cl_2N_2O_2$ and the molecular weight is 305.20. The structural formula is:

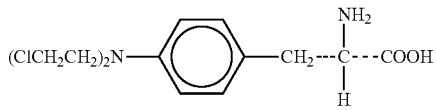

U.S. Pat. No. 4,997,651 to Stephen et al., discloses two-component pharmaceutical formulation of Melphalan comprising freeze-dried Melphalan hydrochloride and a solvent-diluent comprising a citrate, propylene glycol and ethanol.

U.S patent application No. 2013/0131174 to Castillo et al., discloses a solid lyophilized composition of Melphalan hydrochloride having a pH between 4 and 6.

U.S patent application Nos. 2010/0311838, 2014/0213650 and 2014/0221488 disclose parenteral compositions comprising Melphalan and a cyclodextrin derivative.

RU2060031 discloses parenteral lyophilized formulation comprising a Melphalan, polyvinylpyrrolidone, ascorbic acid, glutamic acid, hydrochloric acid and D-mannitol.

The commercial formulation of injectable Alkeran® consists of two components comprising of Melphalan hydrochloride and polyvinylpyrrolidone lyophilized and a diluent comprising a mixture of sodium citrate, water for injection, propylene glycol and ethanol.

The Alkeran® to be infused must be diluted to not more than 0.45 mg/ml in normal saline and infused over 15 minutes.

The reconstitution of the lyophilized product is clinically inconvenient and the lyophilization process is time consuming and often incurs significant expense. Hence, there is a strong need to develop alternate formulations of Melphalan.

The inventors have developed ready to use liquid formulation of Melphalan which overcomes the disadvantages of the formulations reported in prior art.

SUMMARY OF THE INVENTION

One object of the invention provides ready to use liquid parenteral formulation of Melphalan.

Another aspect of the present invention is to provide ready to use liquid parenteral formulation comprising Melphalan, one or more solvents, anti-oxidants and other pharmaceutically acceptable adjuvants thereof.

Yet another aspect of the present invention provides method for preparing ready to use liquid parenteral formulation of Melphalan comprising Melphalan Hydrochloride, one or more solvents, anti-oxidants and other pharmaceutically acceptable adjuvants thereof.

DETAILED DESCRIPTION OF THE INVENTION

In the context of this invention "Melphalan" refers to the pharmaceutically acceptable salts, solvates, hydrates and anhydrous forms thereof, preferably Melphalan Hydrochloride.

As used herein, "ready to use" Melphalan formulations refers to formulations that contain Melphalan in dissolved or solubilized form and are intended to be used as such or upon further dilution in intravenous diluents.

In one embodiment, ready to use liquid parenteral formulations of Melphalan comprise
i. Melphalan,
ii. one or more solvents,
iii. anti-oxidants,
optionally other pharmaceutically acceptable adjuvants thereof.

In yet another embodiment, ready to use liquid parenteral formulations of Melphalan comprise
i. Melphalan Hydrochloride,
ii. one or more solvents selected from the group comprising of dimethylacetamide, polyethylene glycol, ethanol, propylene glycol and glycerine,
iii. anti-oxidants selected from monothioglycerol, L-cysteine, ascorbic acid and
optionally other pharmaceutically acceptable adjuvants thereof.

The composition according to the present invention is intended to be stored at a temperature of 2-8° C.

Suitable solvents include, but are not limited to dimethylacetamide (DMA), dimethyl sulfoxide (DMSO), N-methylpyrrolidone, dimethylisosorbide, ethanol, propylene glycol, glycerine, polyethylene alcohol, propylene glycol esters, polyethylene glycols and the like. Preferred solvents are dimethylacetamide (DMA), ethanol, polyethylene glycols (PEG), glycerine and propylene glycol.

The pharmaceutical compositions of the present invention also contain one or more anti-oxidants selected from the group, but not limited to butylated hydroxyanisole (BHA), butylated hydroxyl toluene (BHT), citric acid, lactic acid, benzoic acid, tocopherol (Vitamin E), ethylenediaminetetraacetic acid, sodium metabisulfite, sodium bisulfite, monothioglycerol, ascorbic acid and their esters, L-cysteine, parabens, benzyl alcohol, propyl gallate, thioglycolic acid, tartaric acid, phosphoric acid, gluconic acid, thiodipropionic acid, acetonic dicarboxylic acid, amino acids such as histidine, cysteine, tryptophan, tyrosine; chelating agents and the like. Most preferred anti-oxidant is monothioglycerol.

The formulation of the present invention may additionally contain buffers, pH adjusting agents, stabilizers such as, but not limited to citrate buffer, glutamate, dicarboxylic acid, lecithin, di(hydroxyethyl)glycine, sorbitol, bicarbonate, tartrate, benzoate, lactate, gluconate, glycine, TRIS buffer, acetate buffer, boric acid buffer, phosphate buffer, amino acids, meglumine and the like.

Solubility studies were carried out with various solvents at 25° C. temperature, to check the solubility of Melphalan hydrochloride. The data is summarized in table 1:

TABLE 1

Solubility studies in various solvents

| Qty of Melphalan Hydrochloride | Quantity of solvents | | | | Result |
|---|---|---|---|---|---|
| | DMA | PEG-400 | Propylene Glycol | Ethanol | |
| 100 mg | 1.1 mL | — | — | — | Clear |
| 100 mg | 0.5 mL | — | — | 0.5 mL | Clear |
| 100 mg | — | — | 1 mL | — | Not Clear |
| 100 mg | — | — | — | 1 mL | Hazy solution |
| 100 mg | 0.3 mL | — | 0.05 mL | 0.65 mL | Clear |
| 100 mg | — | 1.0 mL | 0 mL | — | Clear after vigorous mixing |
| 100 mg | — | 0.9 mL | 0.1 mL | — | Clear |
| 100 mg | — | 0.7 mL | 0.3 mL | — | Clear |
| 100 mg | — | 0.5 mL | 0.5 mL | — | Clear |
| 100 mg | — | 0.2 mL | 0.8 mL | — | Clear |
| 100 mg | — | 0.1 mL | 0.9 mL | — | Clear |

In one of the preferred embodiment, ready to use liquid parenteral formulations of Melphalan comprise:

| i. | Melphalan Hydrochloride | 1 to 30% |
|---|---|---|
| ii. | dimethylacetamide or polyethylene glycol | 20 to 95% |
| iii. | ethanol | 0 to 50% |
| iv. | propylene glycol. | 5 to 50% |
| v. | monothioglycerol | 0.05 to 5% | by weight of the composition.

The invention further relates to a process of preparing liquid formulations of Melphalan. The process comprises:
i. Addition of Melphalan to the manufacturing vessel containing solvent and stirred till a clear solution is obtained.
ii. Addition of remaining solvents to the above solution and stirred.
iii. Addition of anti-oxidant to the solution and stirred till a homogenous solution is obtained.
iv. Filtering and filling the solution in to suitable containers or vials.

Melphalan formulation prepared according to the invention was tested for stability at various stability conditions such as 2-8° C. and 25° C./60% RH for a period of 6 months. Stability data is summarized in table 2.

TABLE 2

Stability data for the product obtained from Example 5

| Condition | | 2-8° C. | | | 25° C./60% RH | |
|---|---|---|---|---|---|---|
| Time point | Initial | 1M | 3M | 6M | 1M | 3M | 6M |
| Assay By HPLC (%) | 99.2 | 97.8 | 97.7 | 96.8 | 97.2 | 94.0 | 90.1 |
| Total Impurities (% w/w) | 0.17 | 0.24 | 0.32 | 0.75 | 0.89 | 2.26 | 4.33 |

Surprisingly no significant increase in total impurities was observed even at 25° C./65% RH. The inventors have found that liquid pharmaceutical formulation of Melphalan comprising of one or more solvents selected form DMA, Ethanol, PEG and propylene glycol in the presence of an anti-oxidant yields a stable liquid formulation of Melphalan overcoming the disadvantages associated with prior art.

Comparative dilution studies were performed to check the stability of the diluted formulations. Melphalan formulation prepared according to the invention was diluted with 0.9% NaCl to get concentration of 0.45 mg/mL. Alkeran® vial (Batch No: P283) was considered as reference for comparative dilution study. Stability of the diluted product was studied at 0 minutes, 30 mins and 60 min. The stability data of the invention formulation and reference product is summarized in table 3.

TABLE 3

Comparative dilution study of the invention formulation with reference product
Dilution study with 0.9% NaCl

| Formulation | Invention formulation after dilution with 0.9% NaCl | | | Reference product after reconstitution with diluent, followed by dilution with 0.9% NaCl | | |
|---|---|---|---|---|---|---|
| Time point | Initial | 30 min | 60 min | Initial | 30 min | 60 min |
| Assay (%) | 97.3 | 97.6 | 95.2 | 95.6 | 91.1 | 88.2 |
| pH of Solution | 3.51 | 3.48 | 3.48 | 5.83 | 6.06 | 6.35 |
| Osmolality (mOsm/kg) | 352 | 348 | 354 | 1120 | 1119 | 1122 |

TABLE 3-continued

Comparative dilution study of the invention formulation with reference product
Dilution study with 0.9% NaCl

| Related Substances | Impurities % (w/w) | | | | | |
|---|---|---|---|---|---|---|
| Impurity D | 1.23 | 3.31 | 5.35 | 1.11 | 3.67 | 5.73 |
| Impurity G | 0.14 | 0.15 | 0.17 | 0.49 | 0.52 | 0.51 |
| Total Impurities | 1.6 | 3.8 | 5.8 | 1.94 | 5.08 | 7.65 |

Surprisingly Melphalan formulation prepared according to the invention showed better stability profile compared to the reference product.

The following examples further describe certain specific aspects and embodiments of the present invention and demonstrate the practice and advantages thereof.

Example 1

| Ingredients | Qty/vial (mg) |
|---|---|
| Melphalan Hydrochloride | 20-200 |
| N,N,Dimethyl acetamide | 350-490 |
| Ethanol | 200-280 |
| Propylene glycol | 180-270 |
| Monothioglycerol | 3-8 |

Manufacturing Process

Melphalan Hydrochloride was added to the manufacturing vessel containing N, N, Dimethyl acetamide and ethanol and stirred to get a clear solution. Propylene glycol was added, followed by the addition of monothioglycerol and stirred to get homogenous solution. The obtained solution was filtered and filled in vials followed by capping and sealing.

Melphalan formulation prepared according to the invention was tested for stability at various stability conditions such as 2-8° C. and 25° C./60% RH for a period of 6 months. Stability data is summarized in table 4.

TABLE 4

Stability data for the product obtained from Example 1

| Condition | | 2-8° C. | | | 25° C. | |
|---|---|---|---|---|---|---|
| Time point | Initial | 1M | 3M | 6M | 1M | 3M | 6M |
| Assay By HPLC (%) | 100.3 | 100.3 | 103.3 | 98.3 | 99.5 | 101.1 | 94.4 |
| Total impurities | 0.19 | 0.16 | 0.20 | 0.63 | 0.30 | 1.60 | 4.37 |

*RT: Relative Retention Time

Example 2

| Ingredients | Qty/vial (mg) | Qty/vial (mg) | Qty/vial (mg) |
|---|---|---|---|
| Melphalan Hydrochloride | 20-200 | 20-200 | 20-200 |
| N,N,Dimethyl acetamide | 380 | 380 | 380 |
| Ethanol | 240 | 320 | 280 |
| Propylene glycol | 310 | 210 | 260 |
| Monothioglycerol | 2.53 | 5.05 | 5.05 |

Manufacturing Process

Melphalan Hydrochloride was added to the manufacturing vessel containing N,N,dimethyl acetamide and ethanol and stirred to get a clear solution. Propylene glycol was added, followed by the addition of monothioglycerol and stirred to get homogenous solution. The obtained solution was filtered and filled in vials followed by capping and sealing.

Example 3

| Ingredients | Qty/vial (mg) |
|---|---|
| Melphalan Hydrochloride | 20-200 |
| Polyethylene glycol | 570 |
| Ethanol | 240 |
| Propylene glycol | 210 |
| Monothioglycerol | 5.05 |

Manufacturing Process

Melphalan Hydrochloride was added to the manufacturing vessel containing polyethylene glycol and ethanol and stirred to get a clear solution. Propylene glycol was added, followed by the addition of monothioglycerol and stirred to get homogenous solution. The obtained solution was filtered and filled in vials followed by capping and sealing.

Example 4

| Ingredients | Quantity/vial (mg) |
|---|---|
| Melphalan Hydrochloride | 20-200 |
| Polyethylene glycol-400 | 490-620 |
| Propylene glycol | 320-390 |
| Monothioglycerol | 5.05 |

Manufacturing Process

Melphalan Hydrochloride was added to the manufacturing vessel containing polyethylene glycol. Propylene glycol was added, followed by the addition of monothioglycerol and stirred to get homogenous solution. The obtained solution was filtered and filled in vials followed by capping and sealing.

Example 5

| Ingredients | Quantity/vial (mg) |
|---|---|
| Melphalan Hydrochloride | 20-200 |
| Polyethylene glycol-400 | 590-950 |
| Propylene glycol | 120-420 |
| Monothioglycerol | 5-8 |

Manufacturing Process

Melphalan Hydrochloride was added to the manufacturing vessel containing polyethylene glycol. Propylene glycol was added, followed by the addition of monothioglycerol and stirred to get homogenous solution. The obtained solution was filtered and filled in vials followed by capping and sealing.

We claim:
1. A stable, liquid parenteral formulation consisting of

| (i) | melphalan hydrochloride | 1 to 30% |
|---|---|---|
| (ii) | dimethylacetamide or polyethylene glycol | 20 to 95% |
| (iii) | ethanol | 0 to 50% |
| (iv) | propylene glycol. | 5 to 50% |
| (v) | monothioglycerol | 0.05 to 5% | by weight of the composition.

2. The formulation of claim 1 wherein the pH of the formulation is between 2 to 5.

3. A stable, liquid parenteral formulation consisting of

| (i) | melphalan hydrochloride | 1 to 30% |
|---|---|---|
| (ii) | polyethylene glycol | 20 to 85% |
| (iii) | ethanol | 0 to 50% |
| (iv) | propylene glycol | 5 to 50% |
| (v) | monothioglycerol | 0.05 to 5% | by weight of the composition.

4. The formulation of claim 3 wherein the pH of the formulation is between 2 to 5.

* * * * *

UNITED STATES PATENT AND TRADEMARK OFFICE
CERTIFICATE OF CORRECTION

PATENT NO. : 10,537,520 B2  
APPLICATION NO. : 15/739034  
DATED : January 21, 2020  
INVENTOR(S) : Chandrashekhar et al.

Page 1 of 1

It is certified that error appears in the above-identified patent and that said Letters Patent is hereby corrected as shown below:

In the Claims

Column 8, Line 6: Claim 1, Delete "(ii) dimethylacetamide or polyethylene glycol 20 to 95%" and insert -- (ii) dimethylacetamide 20 to 85% --

Signed and Sealed this
Twenty-fifth Day of February, 2020

Andrei Iancu
*Director of the United States Patent and Trademark Office*